United States Patent [19]
Lombardo

[11] Patent Number: 5,755,723
[45] Date of Patent: May 26, 1998

[54] RETROGRADE SURGICAL INSTRUMENT

[75] Inventor: Giuseppe Lombardo, Winston-Salem, N.C.

[73] Assignee: TNCO, Inc., Whitman, Mass.

[21] Appl. No.: 843,554

[22] Filed: Apr. 18, 1997

[51] Int. Cl.$^6$ .................................... A61B 17/32
[52] U.S. Cl. ...................... 606/170; 606/83; 606/174
[58] Field of Search .................... 606/79, 83, 167, 606/170, 174, 205, 207, 208

[56] References Cited

U.S. PATENT DOCUMENTS

| | | | |
|---|---|---|---|
| 5,286,255 | 2/1994 | Weber | 604/22 |
| 5,443,475 | 8/1995 | Auerbach et al. | 606/170 |
| 5,571,131 | 11/1996 | Ek et al. | 606/184 |
| 5,609,601 | 3/1997 | Kolesa et al. | 606/170 |

*Primary Examiner*—Michael Buiz
*Assistant Examiner*—David O. Reip
*Attorney, Agent, or Firm*—Stephen Y. Chow; Perkins, Smith & Cohen, LLP

[57] ABSTRACT

A handle-activated retrograde endoscopic instrument with an extension shaft rotatably connected to a fixed handle, the rotation limited by a spring-loaded lock into shaft detents corresponding to rotational position options, and with an extension of an outer tip and reduction of open range of effector movement to shield any pinch area.

5 Claims, 8 Drawing Sheets

RETROGRADE SURGICAL INSTRUMENT

BACKGROUND OF THE INVENTION

The field of the invention is that of micro-instrumentation, that is, articulating, hand-held, instruments used in micro-surgery, electronic micro-assembly and like applications, for grasping, cutting, punching out, probing and the like.

The invention is particularly advantageous for endoscopic, or minimally invasive, surgery, but is also advantageous in other applications for micro-instrumentation.

Figure 1:
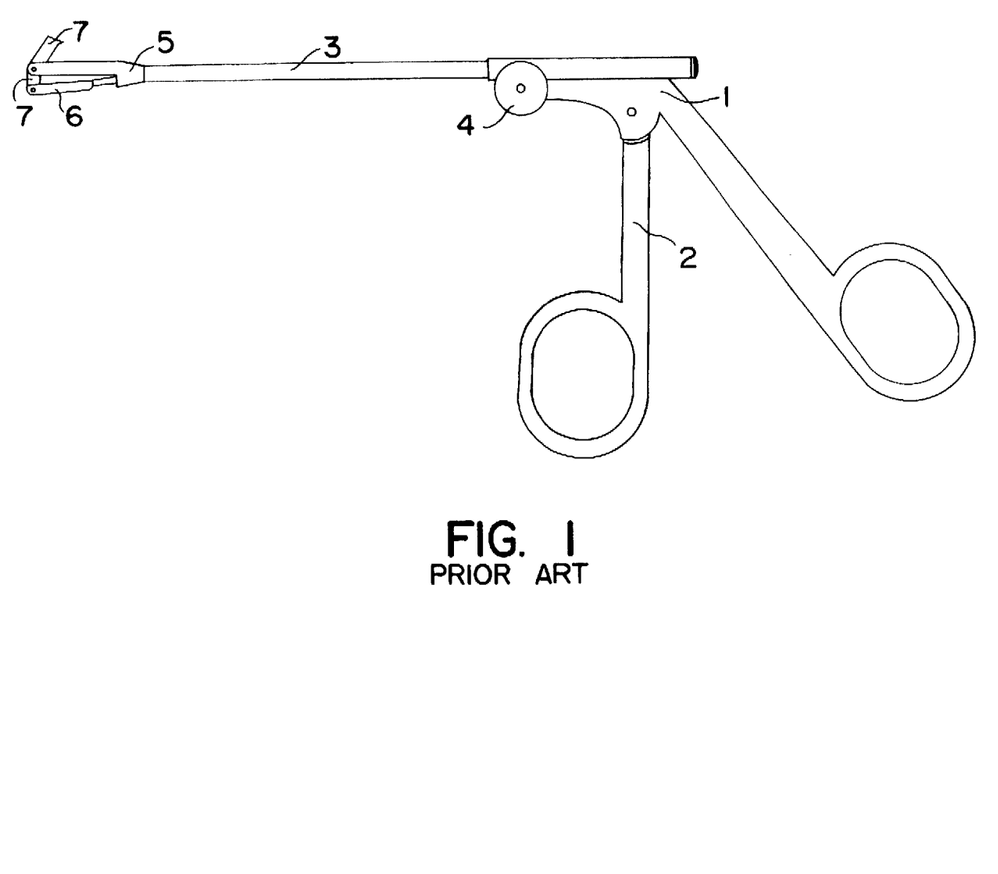
FIG. 1 is a side view of the prior art instrument.

In some situations, as access of an instrument to a region of operation may be in one direction, while the operation is performed to the precise object in substantially a reverse direction. These may be the case, for example, in surgery of the nasal and sinus cavities, in which an instrument may use an operating or effector tip controlled from the end of an access extension shaft passed up through the nasal cavity, while the effector part of the tip, for example, a punch, is directed backwards to directly access tissue at a bend of the cavity. A prior art instrument used for retrograde punching is shown in FIG. 1 in open position, with details of its effector tip shown in FIG. 1A and of its access rotation lock shown in FIG. 1B. Thus, tip assembly 5–7 is inserted through a channel to the operating area using extension shaft 3 and controlled by the fixed handle 1. Then actuating element 6 is pushed forward by pulling back on movable handle 2 (pushing forward an unshown driving rod inside extension shaft 3) to push forward the lower lever portion of effector 7 to close the upper, jaw portion of effector 7 to perform a punching operation with outer tip 5, inside which the jaw fits in closed position. The tip assembly 5–7 and the extension (and unshown drive shaft) may be rotated about the longitudinal axis (through the extension shaft) when a friction collar is loosened by loosening thumb screw 4.

Figure 1A:
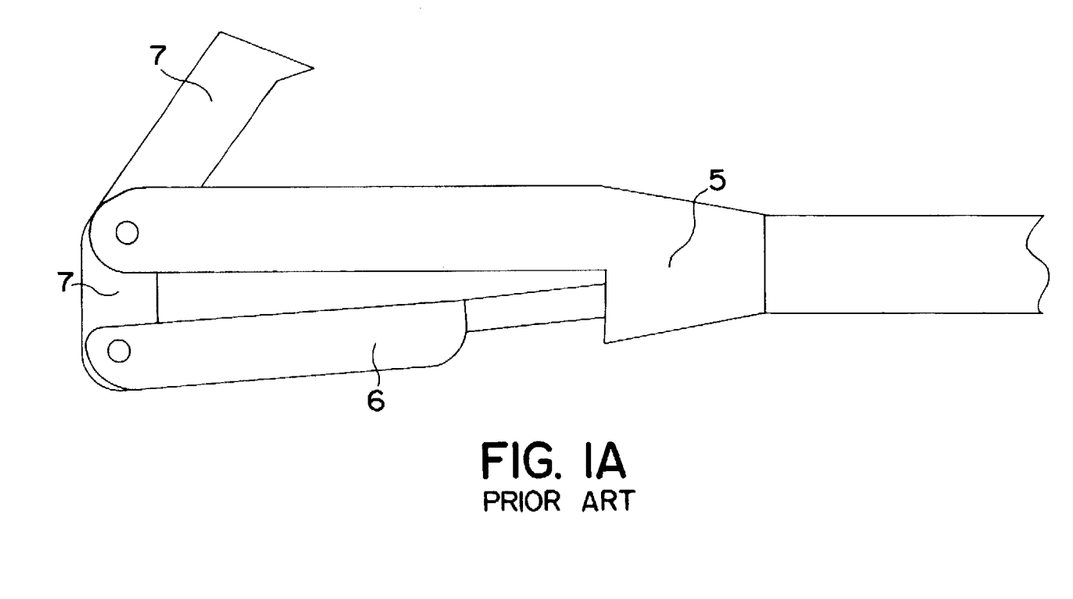
FIG. 1A is a side view of the effector tip portion of the prior art instrument.

Operational disadvantages of the prior art include the trapping of advantical tissue in the gap between actuator 7 and outer tip 5 during a surgical procedure between the time when the effector 7 is in open position, in which the lever arm portion of effector 7 spreads the actuator 6 away from outer tip 5, and the time when effector 7 is in closed position, when actuator 6 engages the bottom of outer tip 5.. The position of this pinching region may not be visible to the surgeon because it can be outside of the operative viewing area. Trapped tissue could limit the range of motion of the cutting jaw necessary to completely cut through tissue. Torn tissue increases the amount of bleeding at an operative site and adds to patient discomfort and recovery time.

Figure 1B:
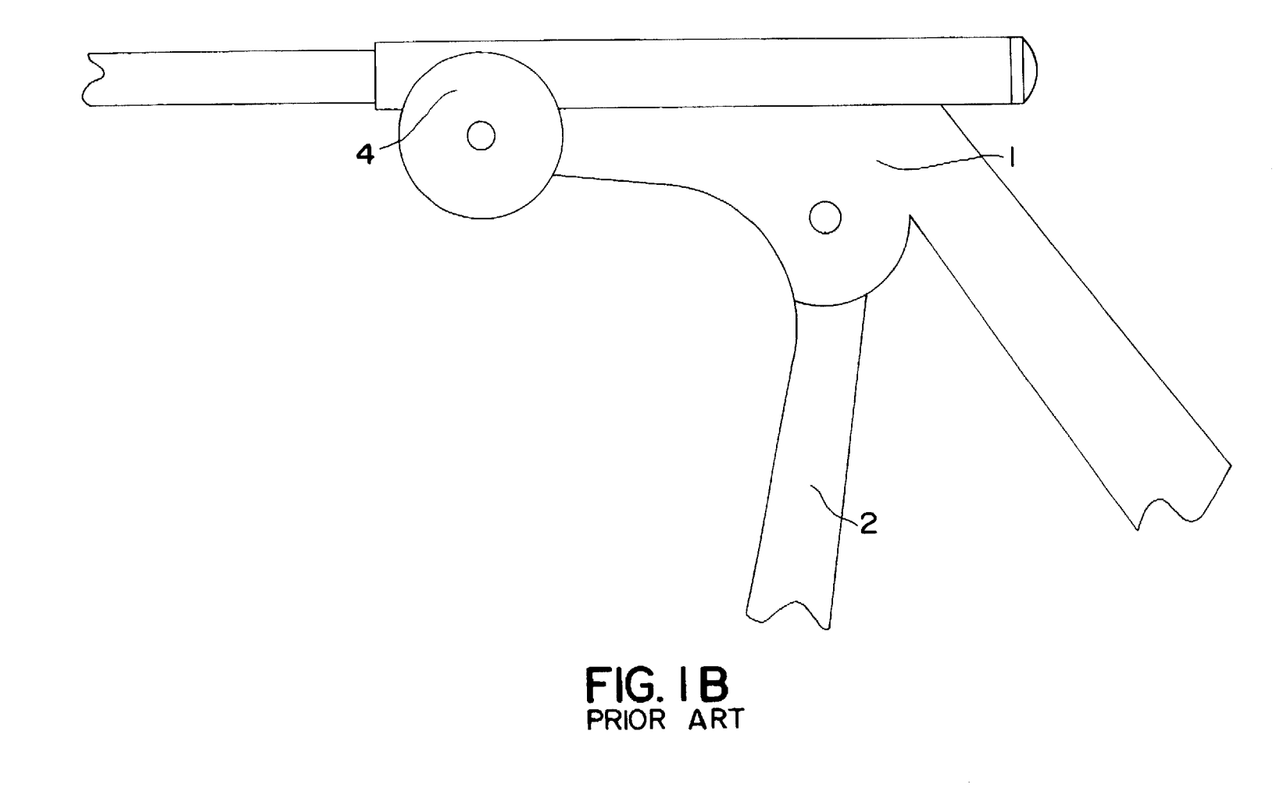
FIG. 1B is a side view of the rotation lock of the prior art instrument.

Another disadvantage of the prior art is the imprecision of the procedure of rotating the extension shaft 3 while the thumb screw 4 is loosened, then tightening the thumb screw 4 when extension shaft 3 is believed to be its desired position. It is possible that the shaft orientation may deviate from the desired plane due to the shaft rotating freely prior to the tightening of the thumb screw. This possibility is heightened if the repositioning procedure is attempted when the tip assembly or shaft is engaging resilient tissue.

SUMMARY OF THE INVENTION

It is a particular objective of the present invention to provide a retrograde endoscopic instrument that avoids unwanted pinching of tissue in its operation.

It is another objective to provide an endoscopic instrument with an effector tip that can rotated to precise rotational positions with the instrument in situ.

The present invention comprises a handle-activated endoscopic instrument with an extension shaft rotatably connected to a fixed handle, the rotation limited by a spring-loaded lock into shaft detents corresponding to rotational position options, and with an extension of an outer tip and reduction of open range of effector movement to shield any pinch area.

DETAILED DESCRIPTION

Figure 2:
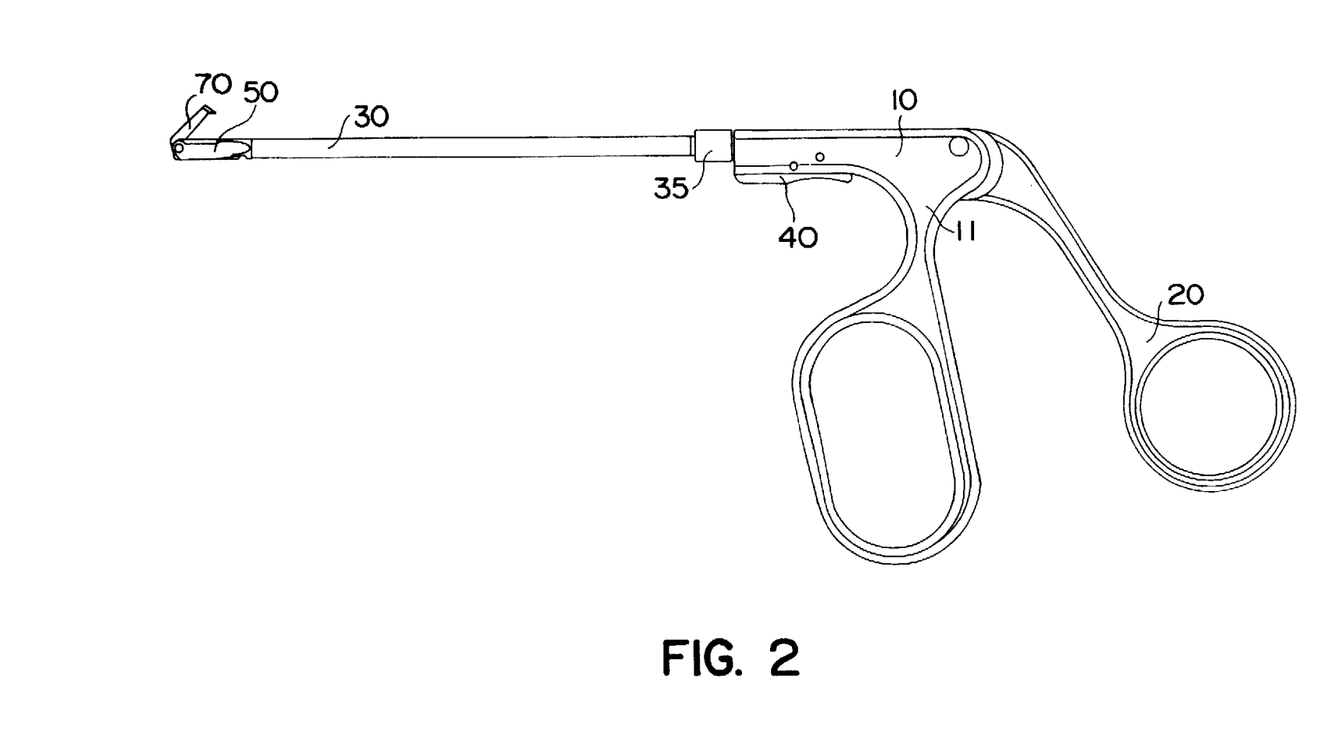
FIG. 2 is a side view of a preferred embodiment of the invention.
Figure 2A:
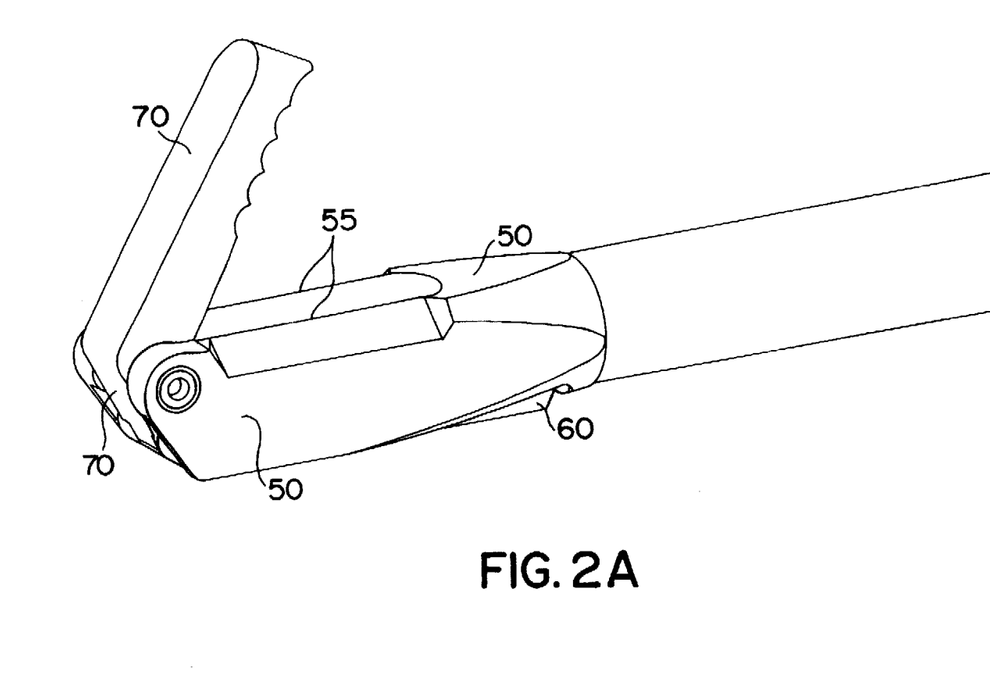
FIG. 2A is a perspective view of the effector tip portion of a preferred embodiment of the invention.

FIG. 2 is a side view of a preferred embodiment of the invention implemented in an endoscopic instrument in which extension shaft 30 is on the order of 3 inches long and 2–3 mm in diameter rotatably mounted on fixed handle assembly 10, which is controlled by the forefinger(s). Handle 20, controlled by the thumb, moves forward (in a linkage not shown) a drive shaft (not shown) and an actuator 60 shown in FIG. 3 (cutaway), and only partially apparent in an exterior side view, such as detailed in FIG. 2A. The actuator 60 moves forward against the lower lever arm of effector 70 to close the upper jaw portion between the cutting edges 55 of the outer tip 50 until limited by stop surface 65 on the actuator 60 (and the actuator 60 is limited by a stop surface ledge 57 on the outer tip).

Figure 3:
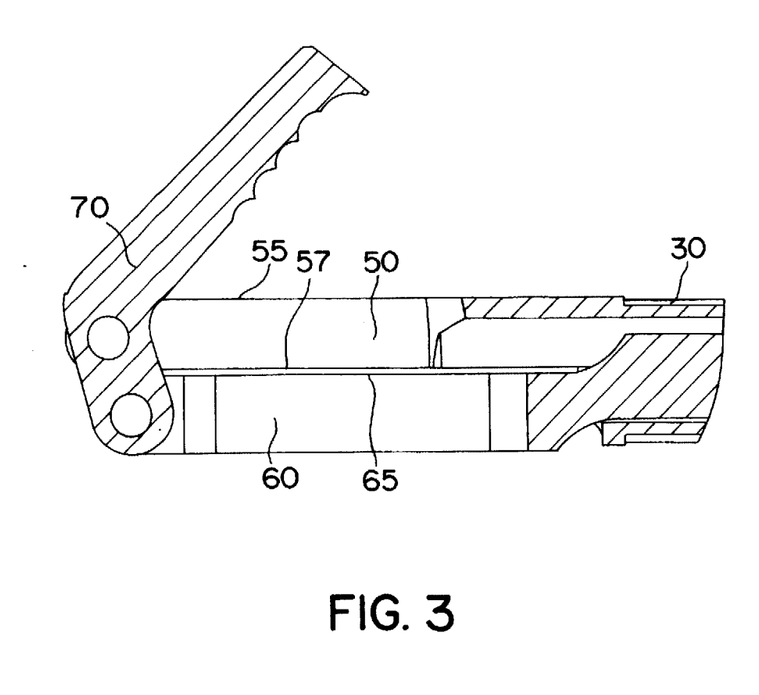
FIG. 3 is a cut-away side view of the effector tip portion of the preferred embodiment of the invention.

Throughout this operation, the top portion of actuator 60 is shielded from contact with tissue by an extension of outer tip 50 down the sides of actuator 60. The configuration is optimized in size for endoscopic surgical applications by reducing the length of the lever portion of effector 70 relative to the prior art, and compensating for mechanical advantage by decreasing the interior angle between the lever and jaw portions by about 30°, thereby limiting the angle that the jaw can be opened to about 60°, instead of 90°. The angular limitation is not considered a disadvantage in operation.

Figure 2B:
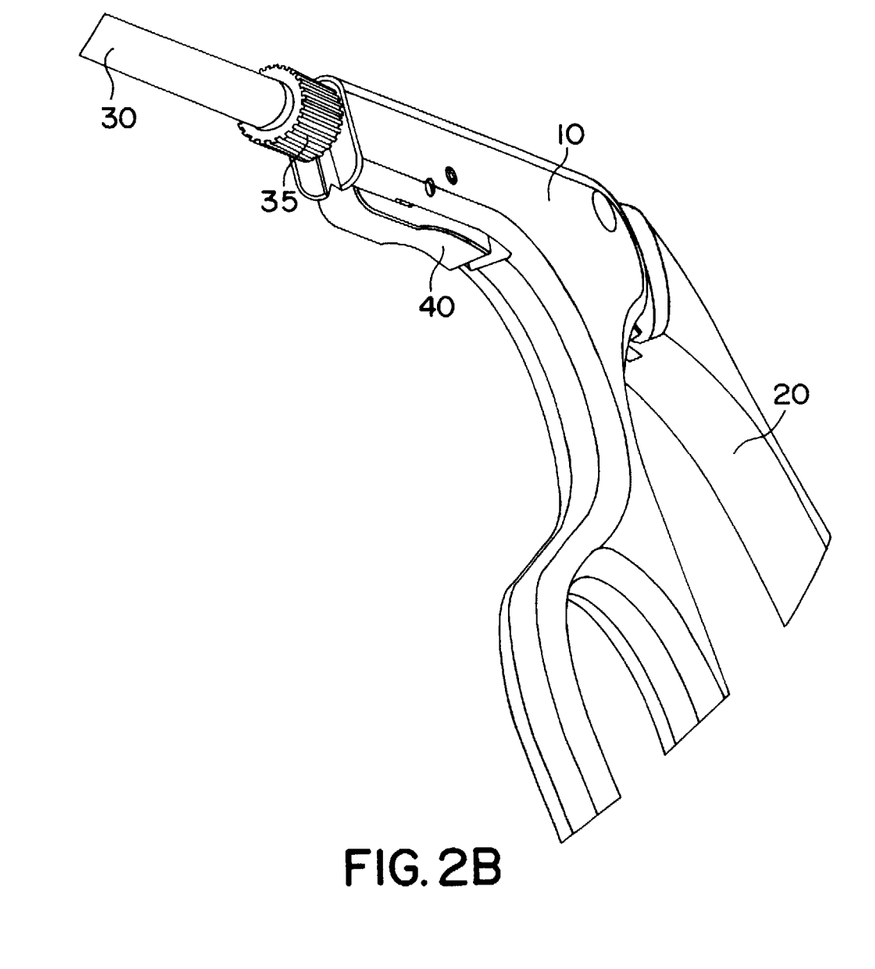
FIG. 2B is a perspective view of the exterior of the rotation lock of the preferred embodiment of the invention.
Figure 4:
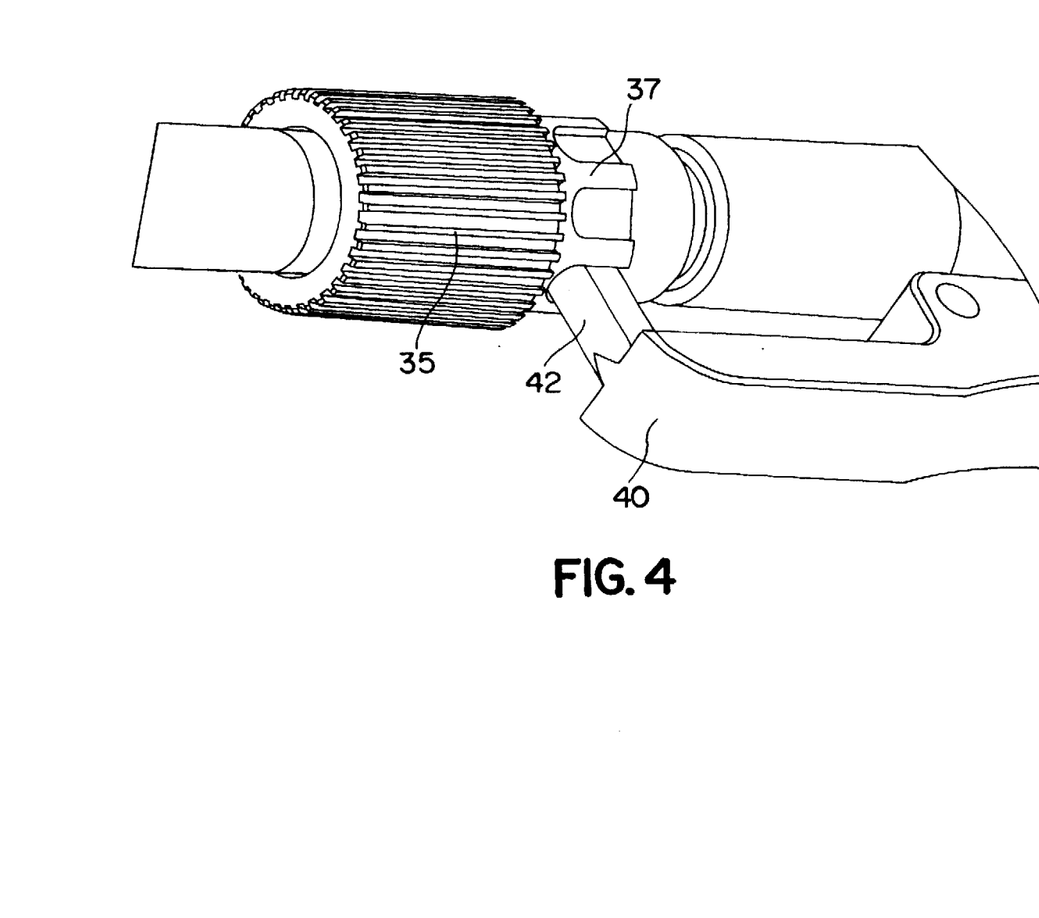
FIG. 4 is a more detailed perspective view of the rotation lock mechanism of the preferred embodiment of the invention

FIG. 2, along with FIGS. 2B and 4, show the rotation lock feature of the invention in a preferred embodiment. The locking mechanism comprises a spring-loaded rocker with a pawl or pin 42 that lifts away from detents 37 on shaft 30 when release lever 40 is pushed upward, for example, by an index finger in the grip area 11 provided by fixed handle assembly 10 (the middle and third fingers may support the fixed handle in the loop structure). When release lever 40 is depressed upwards, tip assembly 50–70 and extension shaft are freely rotatable, preferably using knurled grip 35. At the desired rotational position, release lever 40 is itself released, and pawl or pin 42 is driven into a detent 37 to lock the rotational position.

What is claimed is:

1. A miniature articulated tip tool assembly comprising:
   a handle assembly comprising a fixed handle assembly and a movable handle assembly;
   an extension shaft rotatably mounted on said fixed handle assembly;
   a drive shaft reciprocatingly mounted within said extension shaft and operably linked to said movable handle assembly;
   a rotational locking mechanism comprising detents on said extension shaft corresponding to desired rotational orientation options for said extension shaft, said detents located at a position proximal to said fixed handle assembly, and a disengageable pawl anchored in said fixed handle assembly adapted to engage one of said detents to prevent rotation of said extension shaft; and
   a retrograde effector tip assembly comprising an outer tip rigidly connected to said extension shaft, an effector with a jaw portion pivoted at an end of said effector tip assembly distal said handle assembly and rotatable to a position in which said jaw portion is closed against a portion of said outer tip proximal to said handle assembly from said pivot, and an actuator linkage connected to said drive shaft and to said effector; wherein any open spaces variably defined by components of said effector tip assembly in operation, other than such area defined by said rotation of said jaw, are substantially internal to said outer tip.

2. The apparatus of claim 1 wherein said rotational locking mechanism further comprises a spring-loaded rocker incorporating said disengageable pawl on one end and pivoted on said fixed handle assembly.

3. The apparatus of claim 2 wherein said rotational locking mechanism further comprises a knurled grip on said extension shaft at a location proximal to said fixed handle assembly.

4. The apparatus of claim 1 wherein said effector includes a lever portion at an end of said pivot opposite said jaw portion, said lever portion being part of said actuator linkage along with a rigid activator portion rigidly connected to said drive shaft and connected by a second pivot to said lever portion.

5. The apparatus of claim 4 wherein said lever portion forms an obtuse angle with said jaw portion of approximately 110°.

* * * * *